United States Patent [19]

Amer et al.

[11] Patent Number: 5,522,262
[45] Date of Patent: Jun. 4, 1996

[54] DISPOSABLE SPECIFIC GRAVITY TESTER OF LIQUIDS AND USE THEREOF

[76] Inventors: Moh Samir Amer, P.O. Box 5685, Montecito, Calif. 93013; Jean-Marie Brisset, 15 Rue Olivier Noyer, 75014, Paris, France; Andre Ulmann, 63 Rue Colonie, 75013, Paris, France; Jean P. Delage-Toriel, 6 Rue Auguste Vitu, 75015, Paris, France; Jacques Stemer, 81 Quai D'Orsay, 75007, Paris, France

[21] Appl. No.: 205,073

[22] Filed: Mar. 3, 1994

[51] Int. Cl.$^6$ .................................................. G01N 9/10
[52] U.S. Cl. ........................ 73/440; 128/771; 604/318
[58] Field of Search ................................ 73/440, 864.11; 128/767, 771; 604/318

[56] References Cited

U.S. PATENT DOCUMENTS

| | | | |
|---|---|---|---|
| 1,424,730 | 8/1922 | Linebarger | 73/440 |
| 3,175,553 | 3/1965 | Mattson | 73/440 |
| 3,834,241 | 9/1974 | Garren et al. | 73/864.11 |
| 4,736,628 | 4/1988 | Lin | 73/440 |
| 5,364,595 | 11/1994 | Smith | 73/864.11 |

*Primary Examiner*—John E. Chapman
*Attorney, Agent, or Firm*—Samson B. Leavitt; Michael A. Leavitt

[57] ABSTRACT

A disposable specific gravity tester of liquids such as urine comprising a form-maintaining, flexible or resilient, transparent plastic pipet-type tube, one end of which is integrally closed to form a self-contained bulb, the other normally open end of which is fixedly closed with a solid liquid-permeable plug permitting inward passage there through of the liquid to be tested, and at least one floatable solid testing body in the tube with a predetermined specific gravity at or approximating the expected or normal specific gravity of the liquid; and its method of use, comprising squeezing the bulb while the other plugged end is below the surface of the liquid, releasing the squeezing force to suck up into the tube sufficient liquid to float the testing body or bodies, and observing if and/or which body or bodies sink, float or remain suspended in the liquid.

9 Claims, 1 Drawing Sheet

DISPOSABLE SPECIFIC GRAVITY TESTER OF LIQUIDS AND USE THEREOF

FIELD OF THE INVENTION

This invention relates to means, including a method and disposable apparatus or kit, for measuring or determining, accurately or approximately, the specific gravity of a liquid.

BACKGROUND OF THE INVENTION

Specific gravity determination is one of the routine medical diagnostic tests carried out on several body fluids, most notably urine. In the case of urine, high specific gravity can be indicative of susceptibility to kidney stones, while low specific gravity can diagnose inability to concentrate urine which could underlie other kidney problems.

The specific gravity of urine is inversely related to the urinary output. Maintenance of high urinary output is a therapeutic goal necessary to avoid occurrence of kidney stone disease and/or urinary tract infections. High urinary output reflects sufficient water intake needed to prevent dehydration, a frequent condition in people living in warm climates, frequent airline travelers and in older individuals. Renal stone disease, which is directly related to high urine density, accounts for about 7–10 of every 1000 hospital admissions in the United States.

Normal urinary output varies between 0.25 to 5.0 liters a day depending on the amount of water intake. Urine density can vary accordingly between about 1.001 and 1.030. A urine density of 1.010–1.015 corresponds to an average desirable urinary output and water intake of 1–2 liters per day.

In theory, measurement of daily urinary output is simple. In practice, however, it is very difficult since it necessitates the collection of all the urine excreted during a precise 24 hour period. Thus, it is easier to measure the specific gravity of a urine sample.

Another use of frequent urine density (specific gravity) measurements is to monitor the kidney health of those drinking hard water or water with high salt contents. Hard water intake or prolonged drinking of water with high dissolved salt content increases the work load of the kidneys and can result in kidney stones. The finding of elevated urine specific gravity in those people necessitates replacing their regular water intake with low salt or even distilled water to lower the salt concentration and specific gravity of their urine and to reduce their potential for kidney stones and other kidney problems.

Specific gravity determinations are generally laborious and require the use of expensive and specialized equipment. The methods now available are not suitable for home use. The determination of urine specific gravity at home is needed to frequently monitor the water intake of patients on certain treatments or to follow up their conditions and/or the effectiveness of their treatments. Most importantly, specific gravity determinations are needed to monitor daily water intakes in kidney-stone-susceptible populations. Repeated urinary density measurements are necessary to ensure a permanent and persistent high daily urinary volume and water intake.

OBJECTS OF THE INVENTION

It is an object of this invention to provide an easy, quick, simple and inexpensive method of determining the specific gravity of any liquid, especially urine, in the home or office.

Another object of the invention is to provide such a method to determine whether such liquid has a specific gravity which is above, below or within acceptable maximum and minimum limits.

Still another object of this invention is the provision of a novel, disposable kit, tester, apparatus, equipment, or device for conducting the aforesaid methods.

Other objects and advantages will appear as the description proceeds.

SUMMARY OF THE INVENTION

According to certain of its aspects, the attainment of one or more of the above objects is made possible by this invention which at least in part resides in the provision of a disposable specific gravity tester of liquids comprising a form-maintaining flexible, transparent plastic tube, one end of which is normally integrally closed to form a self-contained bulb and the other normally open end fixedly closed with a solid liquid-permeable plug permitting inward passage therethrough of the liquid to be tested, and at least one floatable solid testing body in the tube with a predetermined specific gravity at or approximating the expected or normal specific gravity of the liquid.

The invention further comprises a method of testing the specific gravity of a liquid such as urine with the aforesaid disposable tester comprising compressing together opposite walls of the section of the tube adjacent the closed end to reduce the volume therein prior to or after insertion of the other, plugged end downward below the surface of the liquid to be tested, releasing the compression to permit the said walls to return to their initial form while the plugged end is below said surface whereby liquid is sucked or drawn up through said plug into the tube in a volume corresponding to the reduction in volume produced by the compression and sufficient to float the floatable solid testing body or bodies, and observing whether the body or bodies sink, float or remain suspended in the liquid.

As stated, the specific gravity of the liquids is determined, accurately or approximately as desired, by observing whether such testing body floats, indicating the specific gravity of the liquid to be above (more or higher than) that of the testing body, or sinks, indicating the specific gravity of the liquid to be below (less or lower than) that of the testing body. If a testing body remains submerged or suspended below the surface and above the bottom of the liquid being tested, the specific gravities of the testing body and liquid being tested can be considered to be substantially the same. The testing body material should of course be sufficiently inert or resistant to the liquid being tested (e.g. urine) to permit observing whether the body sinks or floats.

According to a further embodiment of this invention, the tester may contain a first such body with a specific gravity below, and another such body with a specific gravity above, the expected or normal specific gravity of such liquid being tested.

According to a still further embodiment of this invention, the tester may contain a plurality, e.g. at least 2 such bodies with mutually different specific gravities (different from each other) and above, and at least 2 such bodies with specific gravities different from each other and below, the expected or normal specific gravity of the liquid being tested.

Preferably, each testing body is visibly different or distinguishable from each other body with a different specific gravity, as by being colored, sized or shaped differently.

BRIEF DESCRIPTION OF THE DRAWINGS

Preferred means of attainment of one or more of the objects of this invention are explained and illustrated in the foregoing and following description and the accompanying drawings in which like reference characters identify like elements in the several Figures. In the drawings.

DESCRIPTION OF THE PREFERRED EMBODIMENT

Figure 1:
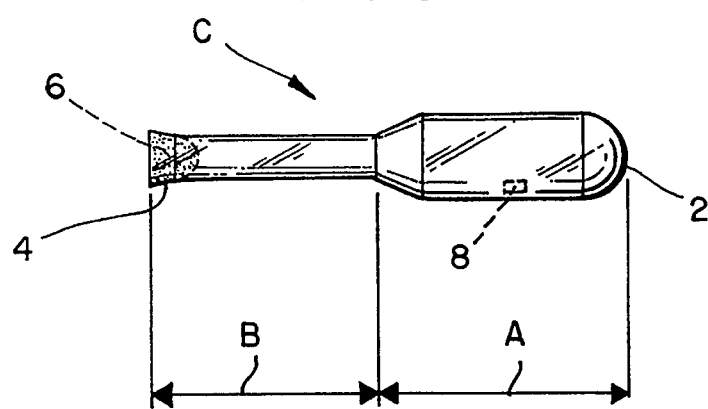
FIG. 1 is a side view, in substantially actual size and dimensions, of a preferred embodiment of the tester device of this invention as supplied to the patient.

In the drawings, A identifies the section adjacent to the closed end 2 and B identifies the section adjacent the other, normally open end 4 of the form-maintaining flexible transparent polyethylene plastic tube identified generally as C. Section B, commonly referred to as the bulb, is squeezable, flexible, resilient and form-maintaining (like the entire tube C) in that it returns to its original shape after being squeezed or compressed and then released. Section B, roughly 1 5/16 inches in length and ½ inch in diameter, is about equal in length to the roughly 1 7/16 inches of section B which is about ¼ inch in diameter, about half that of section A.

Figure 2:
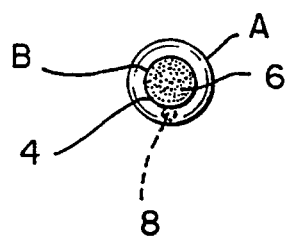
FIG. 2 is an end view, from the left, of FIG. 1.
Figure 3:
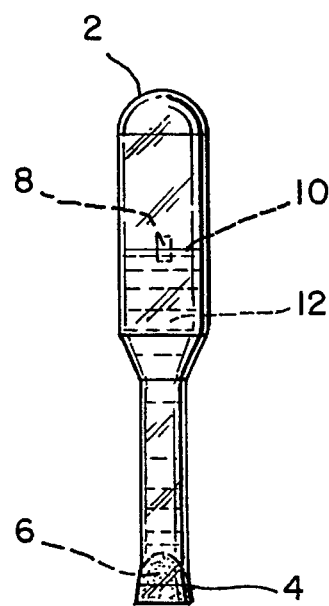
FIG. 3 is an upright view of the tester device of FIG. 1 in use showing a testing body floating in the urine, sucked up into the device.

Normally open end 4 is shown filled, closed or fixedly plugged with bullet shaped or nosed plug 6 of substantially rigid porous liquid-permeable plastic filter material permitting inward (into the bulb end) passage therethrough of the liquid, e.g. urine, being tested. End 4 is shown slightly enlarged, i.e. a bit more than ¼ inch in diameter, as a result of having been heat-softened for insertion therein of rigid bullet-shaped plug 6 with ¼ inch diameter and about 5/16 inch in length. Floatable, solid testing body 8 is shown resting at the bottom of tube C in FIGS. 1 and 2, and floating at the surface 10 of the liquid, e.g. urine in FIG. 3 which indicates that the specific gravity of the urine is higher or more than the specific gravity of testing body 8 which as shown is rod shaped about ⅛ inch long and 3/32 inch in diameter.

The testing bodies of solid material may comprise any type of natural or synthetic material, wood, natural grains such as rosin, and desirably plastics which can by known means be prepared with any desired predetermined specific gravity. The testing material should preferably be resistant or inert to the action of the liquid to be tested, e.g. urine. It may be natural or synthetic, organic, or inorganic, thermosetting or thermoplastic, resins or polymers such as ABS (acrylonitrile/butadience/styrene), nylons, polyetherimides, polyolefins such as polyethylene and polypropylene and their copolymers and alloys, ethylene vinyl acetate copolymers, polystyrenes, SAN copolymers, polycarbonates, polyvinyl chloride, SXNA polycarbonate alloys, polyesters, polyfluoroethylenes, polyesters, thermoplastic elastomers of various types, polyurethanes, urea-, phenol- and melamine-formaldehyde resins, silicones, and other plastics.

Bodies of solid testing material may be in any desired size, shape or color, e.g., beads, pellets, spheres, cubes, flakes, discs, pyramids, stars, round, square, or triangular rod sections, etc., of any convenient size suitable for floating or suspending in the amount of liquid available for testing, and of course large enough to be easily visible in the liquid being tested but not so large as to interfere with each other during testing or as to require a larger amount of liquid being tested than available for such testing. Typically, the smallest dimension could be about 1/16 inch and the largest dimension less than about ½ the diameter of the section of the tube containing the upper level or surface of the liquid being tested. The bodies could have uniform colors, or be variegated, marbleized, striated, or with other patterns, decorations or intelligence providing insignia using any suitable pigments or other coloring material, and could even be hollow. For convenience in describing this invention, bodies of solid testing material will be referred to hereafter as beads, and the liquid to be tested as urine.

Beads of plastic solid testing material are preferred. For example, beads of plastic material with the same or lower specific gravity could be used, and beads with increasing predetermined specific gravities prepared by addition of suitable proportions of increasingly heavier filler material to the melted or fluidized plastic. Many types of such fillers may be employed, for example silica, sand, salts of barium, lead, tin, copper, iron and the like. Increasing amounts of the same filler may be employed to make beads of increasing specific gravities.

Another method of preparing plastic beads with different specific gravities involves simply mixing 2 or more plastic polymeric materials of significantly different known specific gravities in predetermined proportions calculated to provide any specific gravity between the highest and lowest of the plastics being mixed.

If it is only desired to determine whether the specific gravity of the urine is too high or too low, only a single bead need be used with a preset specific gravity at the upper or lower acceptable limit. For example, if the urine is suspected of having a specific gravity about 1.013, a bead with that specific gravity would be added to the urine. If it floats, the urine has a specific gravity above (more than) 1.013. If it sinks, the urine specific gravity is below (less than) 1.013. Similarly, a bead with a specific gravity of 1.001 sinking in urine would indicate a urine specific gravity below 1.001.

It is sometimes desirable to provide the patient or other testing person with a tester with at least two or more, preferably three or four, still more preferably five or more beads, each with different specific gravities ranging from the lowest to the highest expected, which for urine would be between about 1.005 and about 1.025. The beads need not actually be visibly different, in which case the specific gravity of the urine would be determined from the number of beads floating and/or sinking. For example, if the kit contains five beads ranging in specific gravity from 1.005 to 1.025 in increments of 0.005, and all float in the urine, it indicates a specific gravity above 1.025. If only one floats, it would be the 1.005 bead, indicating a urine specific gravity between 1.005 and 1.010. If 2, 3 or 4 float, it indicates a urine specific gravity from, respectively, 1.010 to 1.015, 1.015 to 1.020, and 1.020 to 1.025. If all sink, the urine specific gravity is below 1.005.

The liquid-permeable plug may comprise solid material corresponding to those described above as useful for the floatable testing bodies. The liquid permeability may be provided by piercing or drilling one or more narrow diameter holes through the plug before or after it is fixedly inserted into the normally open end of the tube. Materials for the plug could include materials not suitable as testing bodies, e.g. natural or synthetic sponge, cork, cotton or other fibrous batting or wadding, which could be sufficiently porous to provide the required liquid permeability. In all cases, the plug should be fixedly inserted (e.g. with glue, cement, compression, etc.) into the normally open end of the tube, i.e. non-removable except intentionally, in order to prevent escape of the testing body or bodies from the tube during storage, shipping and transit to the ultimate user.

Preferably the plug comprises rigid porous thermoplastic high density polyethylene plastic with average pore sizes ranging from about 25 to 125 microns, preferably about 85 microns. The porosity is obtained in known manner by heating a mass of thermoplastic plastic particles to melt and bond contacting surfaces of the particles, the porosity increasing with the size of the particles. The plugs are bullet nosed to facilitate insertion thereof into the heat-softened open end of the tube. Such plugs are commercially available from Porex Technologies, 500 Bohannon Road, Fairburn, Ga., USA under the trademarks POREX® and LABPOR® plastic filters and are used to filter out contaminant particles from liquids being sucked up into the tube for examination, testing or transfer.

The form-maintaining, flexible or resilient, transparent plastic tube similarly comprises any of the plastic materials described above as suitable for testing body material provided they can be made as such, i.e. form-maintaining, flexible or resilient and transparent. Most suitable are the polyolefins, e.g. polyethylene, polypropylene, mixtures thereof, and the like. Such tubes are available from and sold by Samco Scientific Incorporated, 1050 Arroyo Ave., San Fernando, Calif. 91340, USA as disposable plastic transfer pipets with closed ends (self-contained bulbs) providing greater efficiency and convenience, no searching for rubber bulbs, no cotton packing, packaging and autoclaving, no need to attach a suction device or change pipet tips, no chance of cross contamination from rubber bulbs, easy disposal, unbreakable, inert to most liquids, etc.

The tester device of this invention may be made by simply inserting the previously prepared testing body or bodies into the open end of the tube with self-contained or built-in bulb adjacent the other end and fixedly inserting the plug into the open end. In the preferred embodiment, the open end of the polyethylene tube is heat-softened and the porous, liquid-permeable high density rigid polyethylene bullet-nosed plug squeeze-fitted into the open end which on cooling contracts around the plug to provide a relatively tight non-removable closure.

The kit to be supplied for household or office use may contain any number of the above-described disposable tester devices, e.g. 1, 6, a dozen, a gross, etc., depending on the condition of the patient, the malady involved, etc. The following examples are illustrative of this invention and are not to be regarded as limitative. All amounts and proportions referred to herein and in the appended claims are by weight unless otherwise indicated.

EXAMPLE 1

Preparation of Plastic Beads

A. Poly (lauryl methacrylate), specific gravity 0.929
B. Poly (methyl methacrylate), specific gravity 1.188

In a heatable container, we mix 68 gm. of A with 32 gm. of B. Heat and stir under vacuum until completely mixed. Allow to cool. Extrude or cast into the desired shape.

| Plastic | Sp. Gr. | | % | | Contribution to Final Sp. Gr. |
| --- | --- | --- | --- | --- | --- |
| A | 0.929 | × | 68 | = | 0.632 |
| B | 1.188 | × | 32 | = | 0.380 |
| | | | | | 1.012 |

Thus, the final mix will have a sp. gr. of 1.012. The use of vacuum is necessary to prevent the inclusion of a variable amount of air with unpredictable effects on the final specific gravity. Different proportions of A and B are employed to produce plastic beads with other desired specific gravities.

EXAMPLE 2

Five plastic beads are prepared as follows:

| Bead | Specific Gravity | Shape |
| --- | --- | --- |
| 1 | 1.005 | tube |
| 2 | 1.010 | ball |
| 3 | 1.015 | disc |
| 4 | 1.020 | plate (0.3" sq. × 0.1" thick) |
| 5 | 1.025 | rod |

All 5 beads are inserted through the left hand open end of the device shown in FIG. 1, the open end fixedly plugged with porous filter material, and the device used to suck up urine into the section adjacent the closed end in sufficient amount to float the beads. Floating of all beads indicates a high specific gravity urine (above 1.025) which may result from low water intake and cause kidney stones. Sinking of beads 1 and 2 establishes a specific gravity between 1.010 and 1.015 which may indicate normal kidney function and sufficient water intake. Sinking of all beads establishes a urine specific gravity below 1.005, indicative of inability to concentrate urine and possibility of existence of other types of kidney disease.

EXAMPLE 3

Clinical Test

Six patients with a propensity for kidney stone formation were tested for urine density or specific gravity using three plastic beads with slightly varying densities approximating 1.013 according to the invention and using a conventional laboratory method (CLM) for comparison. After preliminary testing of their urine densities (Pre), they were asked to drink 1 liter of water and were then later retested (Aft). The number of beads that floated (F) and the number that sank (S) in each test were counted. Results were as follows:

| | Pre | | Aft | |
| --- | --- | --- | --- | --- |
| Patient | Beads | CLM | Beads | CLM |
| 1 | 3F | 1.040 | 3S | 1.010 |
| 2 | 3S | 1.010 | 3S | 1.005 |
| 3 | 3F | 1.030 | 3S | 1.010 |
| 4 | 3F | 1.030 | 3S | 1.010 |
| 5 | 3S | 1.010 | — | — |
| 6 | 1F,2S | 1.015 | — | — |

These results demonstrate the operativeness and reliability of this invention and its clear clinical utility.

This invention has been described with respect to certain preferred embodiments and it will be understood that modifications and variations thereof obvious to those skilled in the art are to be included within the spirit and purview of this invention, application and disclosure and the scope of the appended claims. Thus, if desired, the device need not be disposed of, i.e. after use, the plug could be removed (with the testing body or bodies), the tube rinsed out and preferably dried, and the said body or bodies and plug reinserted.

What is claimed is:

1. A disposable specific gravity tester of urine liquid comprising a form-maintaining, flexible, transparent plastic tube, one end of which is normally integrally closed to form a self-contained bulb and the other normally open end fixedly closed with a solid liquid-permeable porous plug permitting inward passing there through of the liquid to be tested, and at least one floatable solid testing body in the tube with a predetermined specific gravity at or approximating the expected or normal specific gravity of the liquid.

2. A tester according to claim 1 wherein the section of the tube adjacent the closed end has a diameter or width sufficiently larger than that of the section adjacent the other, plugged end to facilitate sucking sufficient liquid into the tube to observe whether or not the testing body floats therein.

3. A tester according to claim 2 wherein the two sections are approximately equal in length.

4. A tester according to claim 3 wherein the diameter or width of the section adjacent the closed end is about 1.5 to 5 times that of the other section adjacent the other plugged end.

5. A tester according to claim 4 wherein the tube contains a plurality of floatable solid testing bodies with mutually different predetermined specific gravities approximating the expected or normal specific gravity of the liquid.

6. A tester according to claim 5 wherein the testing bodies are mutually visibly distinguishable.

7. A tester according to claim 1 which is about 2.5 to about 3 inches in length, and the diameter or width of the section adjacent the closed end is about 0.5 inches and about twice that of the section adjacent the other, plugged end.

8. A tester according to claim 4 which is about 2.5 to about 3 inches in length, and the diameter or width of the section adjacent the closed end is about 0.5 inches and about twice that of the section adjacent the other, plugged end.

9. A method of testing the specific gravity of urine liquid with a tester as defined in any one of claims 1 to 8 comprising compressing together opposite walls of the section of the tube adjacent the closed end to reduce the volume therein prior to or after insertion of the other, plugged end downward below the surface of the liquid to be tested, releasing the compression to permit the said walls to return to their initial form while the plugged end is below said surface whereby liquid is sucked or drawn up through said plug into the tube in a volume corresponding to the reduction in volume produced by compression and sufficient to float the floatable solid testing body or bodies, and observing whether said body or bodies sink, float or remain suspended in the liquid.

* * * * *